United States Patent [19]

Bistrek et al.

[11] Patent Number: 5,117,842
[45] Date of Patent: Jun. 2, 1992

[54] TANNING TETHER APPARATUS

[76] Inventors: Robert A. Bistrek; Cheryl A. Bistrek, both of 929 E. 9th St., Hazelton, Pa. 18201

[21] Appl. No.: 657,147

[22] Filed: Feb. 19, 1991

[51] Int. Cl.⁵ ............................................. A61F 5/37
[52] U.S. Cl. ................................... 128/882; 128/869
[58] Field of Search ............... 128/869, 878, 879, 880, 128/881, 882, 893, 894, DIG. 20

[56] References Cited

U.S. PATENT DOCUMENTS

| | | | |
|---|---|---|---|
| 667,338 | 2/1901 | Rogers | 128/880 X |
| 2,650,590 | 9/1953 | Moore et al. | 128/882 |
| 3,324,851 | 6/1967 | Posner | 128/878 |
| 3,338,237 | 8/1967 | Sconce | 128/DIG. 20 X |
| 4,239,228 | 12/1980 | Norman et al. | 128/878 X |
| 4,688,564 | 8/1987 | Kelly | 128/878 |
| 4,854,138 | 8/1989 | Charland | 128/878 X |
| 5,012,821 | 5/1991 | Tarver | 128/879 X |

Primary Examiner—Robert A. Hafer
Assistant Examiner—Sam Rimell
Attorney, Agent, or Firm—Leon Gilden

[57] ABSTRACT

An apparatus for mounting to opposed interior toes of an individual for containing alignment of the toes during a tanning procedure is provided, wherein a continuous loop includes a plurality of lock cylinders mounted along the loops to define securement loops at each end for securement of an associated toe therewithin. A modification of the invention includes an inflatable cylinder mounted at each end of a flexible line, wherein the inflatable cylinder permits inflation to a predetermined pressure to permit securement of an individual's toe therewithin and the inflation cylinders are transparent and formed of an ultraviolet transmissive material. Further, the invention provides an apparatus for mounting heel support inflatable pads mounted by flexible lines to each end of the tether for positioning an individual's heels thereon for enhanced comfort in use of the organization.

3 Claims, 4 Drawing Sheets

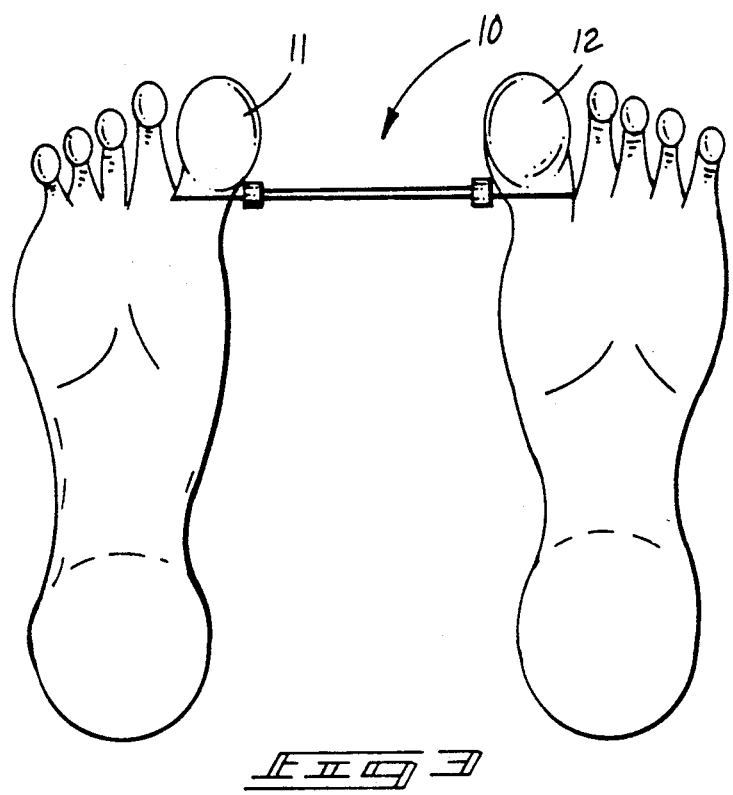
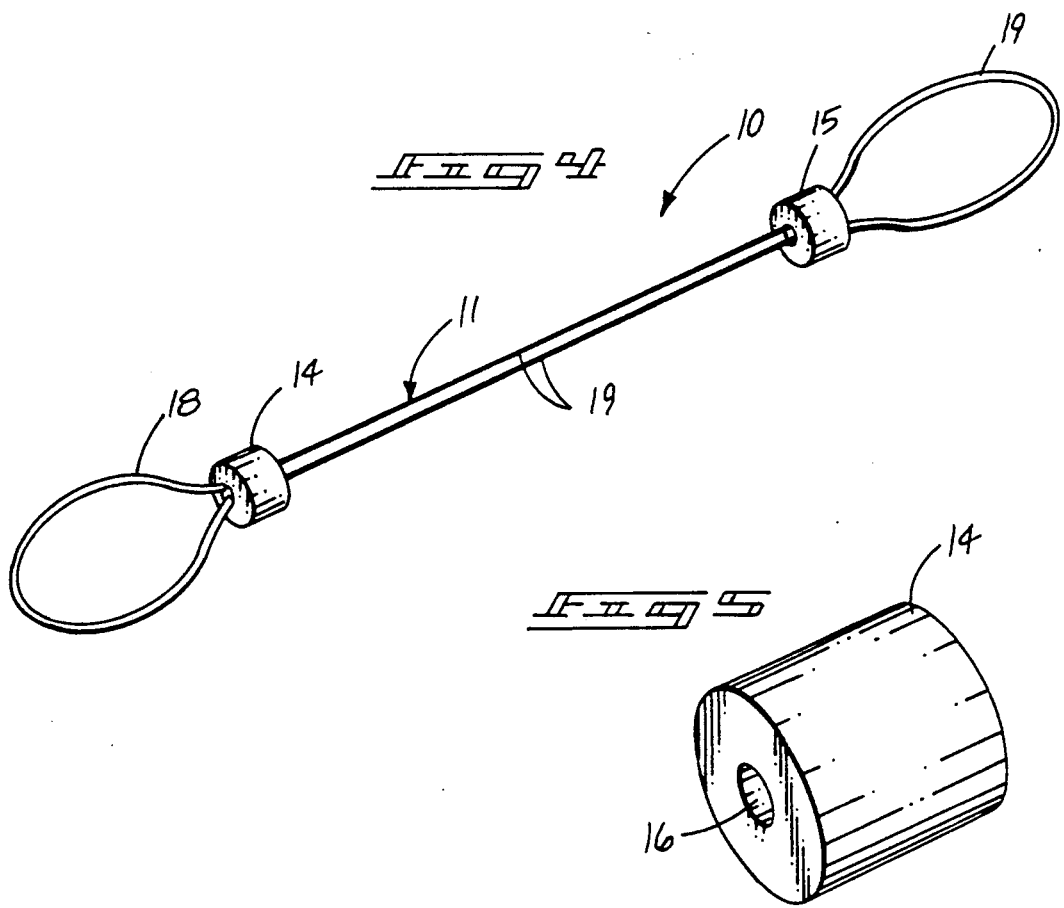

TANNING TETHER APPARATUS

BACKGROUND OF THE INVENTION

1. Field of the Invention

The field of invention relates to tanning apparatus, and more particularly pertains to a new and improved tanning tether apparatus wherein the same secures and aligns an individual's feet during a tanning procedure.

2. Description of the Prior Art

During tanning, an individual is prone to rotate one leg relative to another to thereby provide for displacement of the feet and uneven tanning relative from one leg to the other. The instant invention provides a tether apparatus to effect this procedure. Prior art apparatus for effecting restraining devices may be found in U.S. Pat. No. 4,854,138 to Charland providing a restraining device for use in law enforcement, wherein a plurality of loops are directed through a locking block to secure an individual's wrist through a loop.

U.S. Pat. No. 4,024,736 to De Michieli sets forth a restraint device wherein an elongate tether mounts a locking ring at each end thereof to permit cuffing of an individual and provide limited mobility thereof.

U.S. Pat. No. 1,534,936 to Fischbach sets forth a restraining device wherein a plurality of loops are mounted to each end of a flexible tether line of the restraining device.

As such, it may be appreciated that there continues to be a need for a new and improved tanning tether apparatus as set forth by the instant invention which addresses both the problems of ease of use as well as effectiveness in construction in maintaining and aligning of an individual's feet during a tanning procedure and in this respect, the present invention substantially fulfills this need.

SUMMARY OF THE INVENTION

In view of the foregoing disadvantages inherent in the known types of tanning apparatus now present in the prior art, the present invention provides a tanning tether apparatus wherein the same utilizes a flexible loop mounted between an individual's feet to maintain the feet in alignment during a tanning procedure. As such, the general purpose of the present invention, which will be described subsequently in greater detail, is to provide a new and improved tanning tether apparatus which has all the advantages of the prior art tanning apparatus and none of the disadvantages.

To attain this, the present invention provides an apparatus for mounting to opposed interior toes of an individual for containing alignment of the toes during a tanning procedure, wherein a continuous loop includes a plurality of lock cylinders mounted along the loops to define securement loops at each end for securement of an associated toe therewithin. A modification of the invention includes an inflatable cylinder mounted at each end of a flexible line, wherein the inflatable cylinder permits inflation to a predetermined pressure to permit securement of an individual's toes therewithin and the inflation cylinders are transparent and formed of an ultraviolet transmissive material. Further, the invention provides an apparatus for mounting heel support inflatable pads mounted by flexible lines to each end of the tether for positioning an individual's heels thereon for enhanced comfort in use of the organization.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tanning tether apparatus which has all the advantages of the prior art tanning apparatus and none of the disadvantages.

It is another object of the present invention to provide a new and improved tanning tether apparatus which may be easily and efficiently manufactured and marketed.

It is a further object of the present invention to provide a new and improved tanning tether apparatus which is of a durable and reliable construction.

An even further object of the present invention is to provide a new and improved tanning tether apparatus which is susceptible of a low cost of manufacture with regard to both materials and labor, and which accordingly is then susceptible of low prices of sale to the consuming public, thereby making such tanning tether apparatus economically available to the buying public.

Still yet another object of the present invention is to provide a new and improved tanning tether apparatus which provides in the apparatuses and methods of the prior art some of the advantages thereof, while simultaneously overcoming some of the disadvantages normally associated therewith.

Still another object of the present invention is to provide a new and improved tanning tether apparatus wherein the same utilizes securement members at each end of a flexible tether line to maintain alignment and securement of an individual's feet in an aligned orientation for consistent tanning, as well as providing support pads mounted to further flexible lines to mount an individual's feet thereon during a tanning procedure.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic side view, taken in elevation, of the instant invention mounted to an individual's feet.

FIG. 4 is an isometric illustration of the instant invention.

FIG. 5 is an isometric illustration of a lock cylinder utilized by the invention as set forth in FIG. 4.

DESCRIPTION OF THE PREFERRED EMBODIMENT

Figure 1:
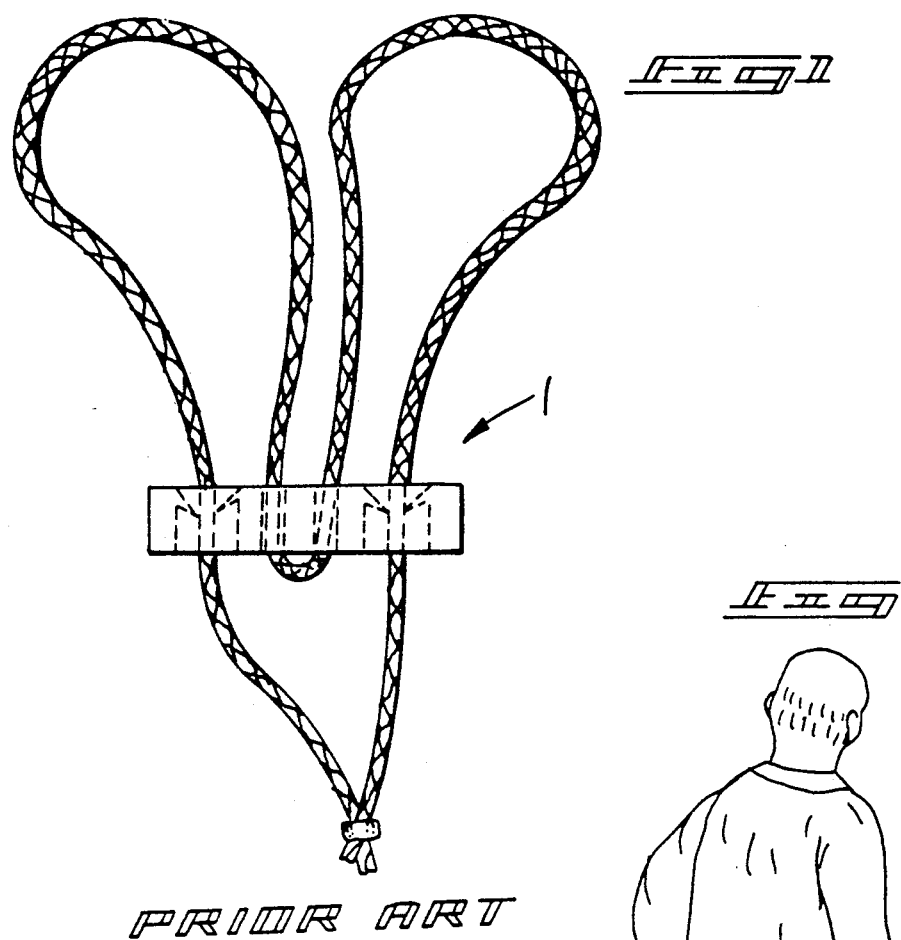
FIG. 1 is an orthographic side view of a prior art restraint device.

With reference now to the drawings, and in particular to FIGS. 1 to 9 thereof, a new and improved tanning tether apparatus embodying the principles and concepts of the present invention and generally designated by the reference numeral 10 will be described.

Figure 2:
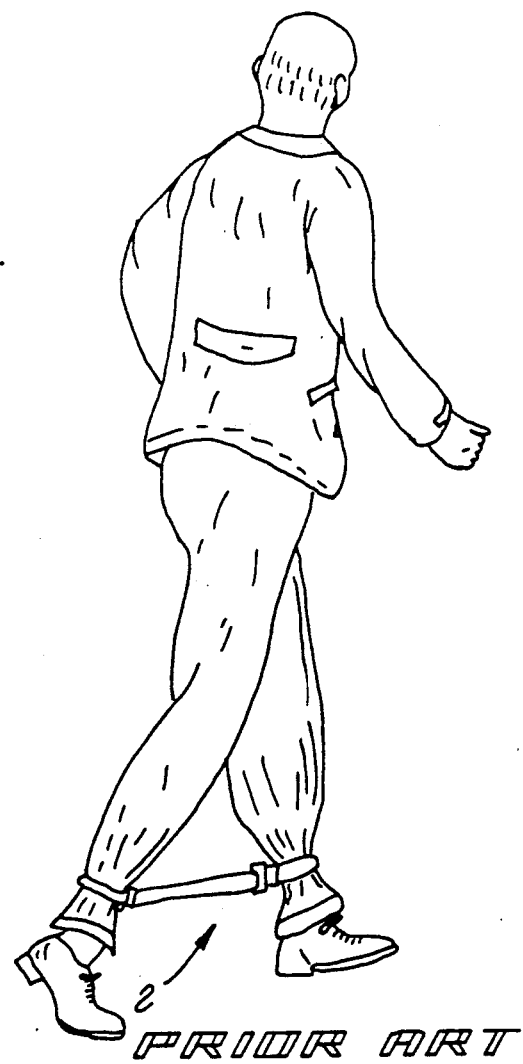
FIG. 2 is an example of a further prior art restraint device.

FIG. 1 illustrates a prior art restraint device 1, wherein a plurality of loops are directed in a locking manner through a locking block for securement of an individual's wrist therethrough in a manner as set forth in U.S. Pat. No. 4,854,138. FIG. 2 sets forth a further example of a prior art restraint device 2, as disclosed in U.S. Pat. No. 4,024,736, utilizing locking cups mounted to each end of a flexible tether line for use as a restraint in securing prisoners in a restrained manner.

More specifically, the tanning tether apparatus 10 of the instant invention essentially comprises a continuous flexible tether line 13 that is mounted through a respective spaced first and second slide lock cylinder 14 and 15. The slide lock cylinders are each defined by a central coaxial bore 16 forming a constricted sliding relationship relative to the tether line 13 directed therethrough. The lock cylinders 14 and 15 define respective right and left loops 17 and 18, with parallel line members 19 formed of the tether line 13 extending between the locked cylinders. The thusly formed loops are mounted to respective right and left large interior toe members 11 and 12 of an individual's feet, as illustrated in FIG. 3, to provide proper positioning of the feet during a sun tanning event.

Figure 6:
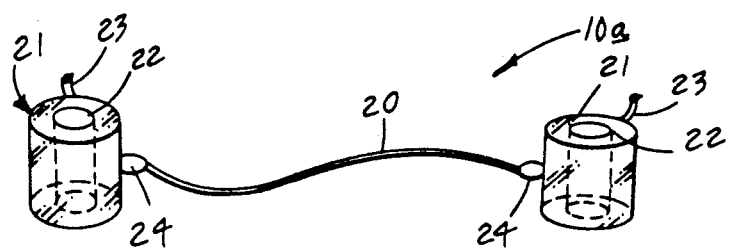
FIG. 6 is an isometric illustration of a modification of the instant invention.

FIG. 6 illustrates the use of a modified apparatus 10a, wherein a single tether line 20 is directed between and secured to opposed distal ends of the tether line 20 to mounting rings 24. The mounting rings 24 are each mounted to a respective transparent, flexible, inflatable cylinder 21 formed with a central toe receiving bore 22 therethrough. The cylinders are formed of a transparent ultraviolet light transmissible material to permit tanning of the toe portions 11 and 12 secured within the respective inflatable cylinders. Each cylinder includes an inflation valve 23 to permit selective inflation to a desired pressure to thereby control a predetermined degree of grasping of each toe within each respective bore.

Figure 7:
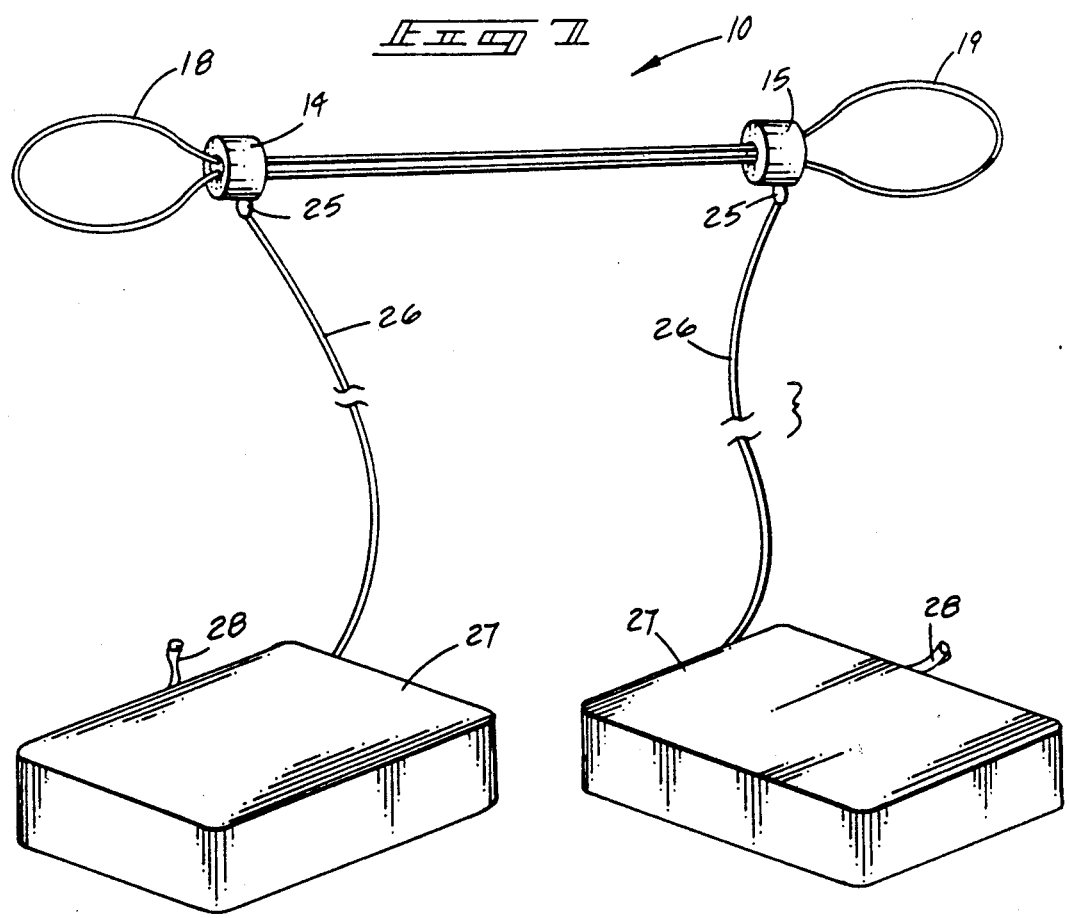
FIG. 7 is an isometric illustration of the tether apparatus utilizing inflatable heel cushions.
Figures 8, 9:
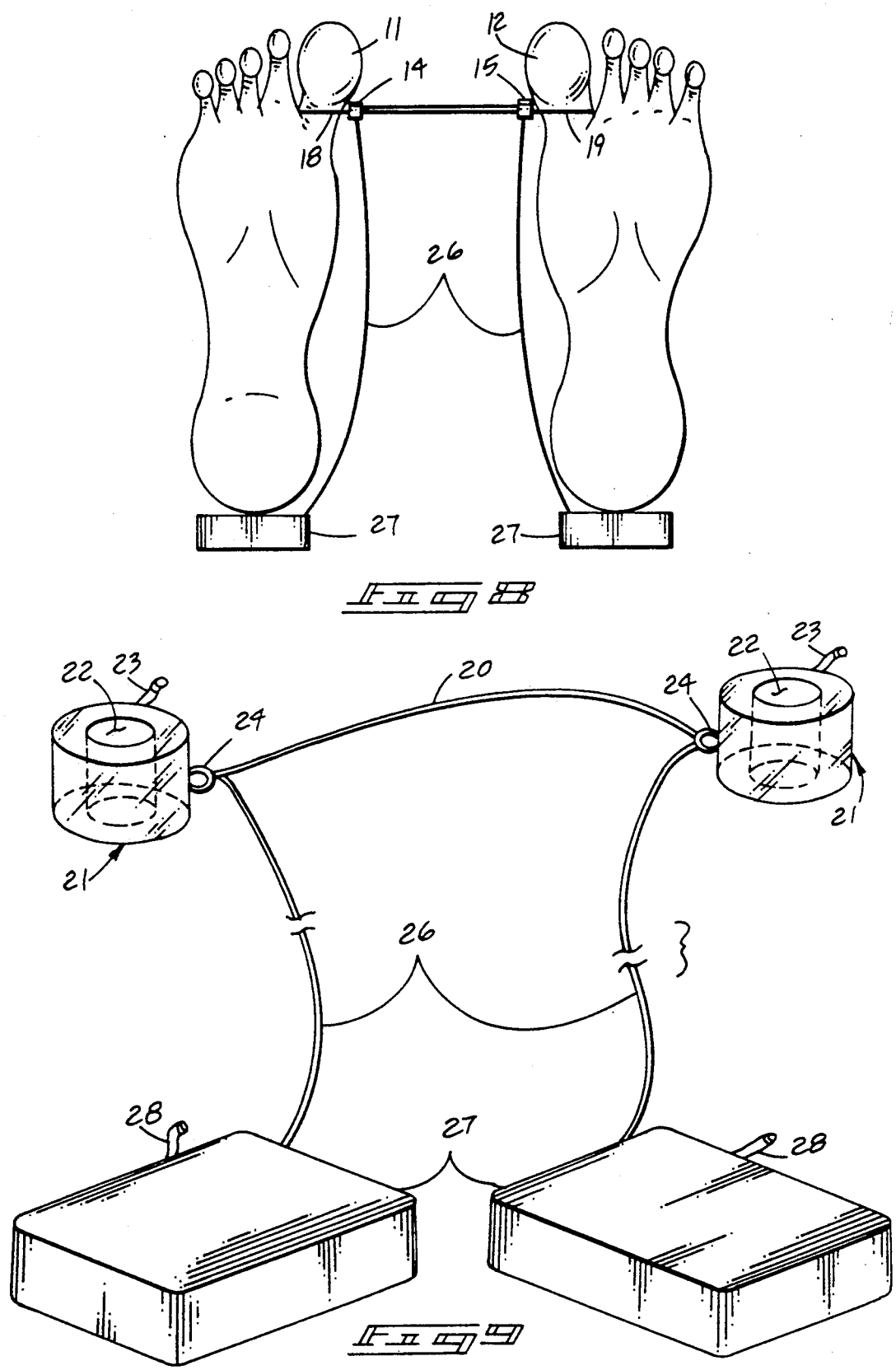
FIG. 8 is an orthographic side view of the apparatus and heel cushions in use.
FIG. 9 is an isometric illustration of the modified tanning tether apparatus in association with the heel cushions.

FIGS. 7 and 8 illustrate the apparatus 10 utilizing an inflatable flexible heel cushion 27, with each heel cushion 27 including a heel cushion inflation valve 28 to permit inflation of each heel cushion to a desired predetermined pressure for resting each heel portion of each foot thereon, as illustrated in FIG. 8 for example, to provide comfort thereto, with a flexible line 26 secured between a respective cylinder support ring 25 mounted to each of the cylinders 14 and 15 thereby securing in a pivotal relationship each flexible line 26 that is secured to each heel cushion 27, with each tether line 26 defined by a predetermined equal length substantially equal to a predetermined spacing from the large toe portions 11 and 12 to the respective heel cushions to further position the heel cushions at a predetermined relationship relative to the loops for proper orientation of the feet during a sun tanning event.

FIG. 9 illustrates the modified apparatus 10a, including the heel cushions 27 mounted thereto, wherein the flexible lines 26 are mounted to the mounting rings 24 of each transparent flexible and inflatable cylinder 21.

It should be further noted that each flexible line 26 is defined by a first length and the tether line 20 is defined by a second length, wherein the first length is greater than the second length to properly orient each heel cushion 27 in a properly spaced relationship relative to each transparent cylinder, and to properly position each of the respective right and left toes 11 and 12 in a narrowed spaced relationship relative to one another to properly align the feet for a tanning event, as illustrated in FIG. 8 for example.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tanning tether apparatus comprising, in combination, an elongate flexible tether line, the tether line including a right and left distal end, each right and left distal end including securement means mounted to the tether line for mounting in a surrounding relationship relative to a respective right and left toe of an individual's foot, and wherein the securement means includes a respective right and left flexible transparent inflatable cylinder, each cylinder including a central toe receiving bore directed therethrough, and each cylinder including a cylinder inflation valve means for effecting selective inflation of each cylinder to a predetermined rigidity to selectively effect a predetermined degree of grasping of a respective toe within each cylinder, and each cylinder including a mounting ring defined by a left mounting ring mounted to the left distal end of the tether line, and a right mounting ring mounted to the right distal end of the tether line, and including a left flexible line mounted to the left mounting ring and a right flexible line mounted to the right mounting ring, and the right flexible line securing a heel cushion remote from the right mounting ring, and the left flexible line including a further heel cushion secured to the left flexible line remote from the right mounting ring, and each heel cushion including a heel cushion inflation valve to effect selective inflation of each heel cushion for receiving a heel portion of an individual's foot thereon.

2. An apparatus as set forth in claim 1 wherein each right and left flexible line is defined by a predetermined first length, and the tether line mounted between the right and left mounting ring is defined by a length equal to a second length, wherein the second length is less than the first length to properly orient each heel cushion relative to each inflatable cylinder.

3. An apparatus as set forth in claim 2 wherein each transparent cylinder is formed of an ultraviolet light transmissible material.

* * * * *